United States Patent

Pretel et al.

Patent Number: 5,845,638

Date of Patent: *Dec. 8, 1998

[54] INSTRUMENT AND METHOD OF MEASURING TORTICOLLIS

[75] Inventors: Maria Pretel, Alisa Viejo; Catherine E. Hoover, Newport Beach; Elaine P. Kelley, Tustin; Judith M. Leon, Laguna Niguel, all of Calif.

[73] Assignee: Allergan, Inc., Irvine, Calif.

[*] Notice: Under 35 U.S.C. 154(b), the term of this patent shall be extended for 30 days.

[21] Appl. No.: 510,526

[22] Filed: Aug. 2, 1995

[51] Int. Cl.⁶ ........................................ A61B 5/103
[52] U.S. Cl. ........................ 128/595; 128/774; 33/512
[58] Field of Search ........................ 128/774, 781, 128/782; 33/512, 511, 381, 382

[56] References Cited

U.S. PATENT DOCUMENTS

| | | | |
|---|---|---|---|
| 4,201,226 | 5/1980 | Phillips | 33/512 |
| 4,483,075 | 11/1984 | Kundin | 33/512 |
| 4,485,825 | 12/1984 | Domjan et al. | 33/512 |
| 4,528,990 | 7/1985 | Knowles | 128/774 |
| 4,777,965 | 10/1988 | Allison et al. | 128/774 |
| 4,848,358 | 7/1989 | Nitzan et al. | 128/782 |
| 4,928,709 | 5/1990 | Allison et al. | 128/782 |
| 5,038,489 | 8/1991 | Muehlenbein | 33/512 |
| 5,188,121 | 2/1993 | Hanson | 128/781 |
| 5,263,492 | 11/1993 | Voyce | 128/782 |
| 5,351,408 | 10/1994 | Street | 33/512 |
| 5,373,857 | 12/1994 | Travers et al. | 128/782 |
| 5,459,676 | 10/1995 | Livingston | 33/512 |

OTHER PUBLICATIONS

Dykstra et. al. Movement Disorders vol. 8 No. 1 1993 pp. 38–42.
Van Hoof et. al. Jour of Neurology vol. 234 pp. 322–327, 1987.
Schatz et. al. Amer. Acad Ophthal & Otol vol. 73 pp. 650–653, 1971.
Ansari, et. al. Neurology Service Jan. 1973 pp. 44–47.
Youdas, et. al. Physical Therapy vol. 71, No. 2 Feb. 1991 pp. 98–104.
Youdas, et al Physical Therapy vol. 72, No. 11, Nov. 1992 pp. 770–780.
Rheault, et. al. JOSPT vol. 15 No. 3 Mar. 1992 pp. 147–149.

Primary Examiner—Michael Buiz
Assistant Examiner—Daphna Shai
Attorney, Agent, or Firm—Walter A. Hackler

[57] ABSTRACT

An instrument and method are provided for the simultaneous measurement of torticollis characteristics, namely, head turn, head tilt and head bend. A vertical protractor is provided for measuring both patient head tilt in a sagittal plane of a patient body and patient head bend in a frontal plane of a patient body. A horizontal protractor provides for measuring patient head turn in a transverse plane of a patient body. When used in combination, the vertical and horizontal protractors provide simultaneous measurement of either head turn or head bend or head turn and head tilt.

14 Claims, 4 Drawing Sheets

INSTRUMENT AND METHOD OF MEASURING TORTICOLLIS

Torticollis is a contracted state of the cervical muscles which produce a twisting of the muscles and an unnatural position of the head. Torticollis may result from a number of conditions, for example, congenital torticollis is due to injury to the sternocleidomastoid muscle on one side at the time of birth and its transformation into a fibrous cord which cannot lengthen with the growing neck. Ocular torticollis is due to a high degree of astigmatism or to ocular muscle palsy. Spasmodic torticollis is that which is due to spasms of certain muscles which occurs intermittently.

Botulinum toxins have been used to treat spasmodic torticollis and in that regard, it is necessary to provide a measurement tool for measuring improvement in the cervical range of motion which can provide objective measurements of improvement in range of motion.

Such measurements are necessary in order to develop a treatment plan, monitor patient progress, and evaluate the effectiveness of the treatment. It is necessary to determine the range of motion about three axes of rotation in order to obtain a complete assessment of a patient's condition.

In addition to photography for documentation of torticollis, many instruments have been developed to measure head turn, head tilt and head bend. Many of these instruments have included means for attaching the device to an individual. Often in these devices, the reproducibility of measurement is difficult since there are no established internal references.

In addition, heretofore attempts to develop measurement devices for cervical range of motion have resulted in intricate apparatus which is not only expensive to produce, but complicated in its operation, often requiring special techniques to be learned by a clinician.

Thus, a simple apparatus and protocol for measuring head turn, head tilt and head bend, preferably in a simultaneous manner, is needed to obtain objective and comparative measurements of cervical range of motion which, in turn, permits objective evaluation of a treatment plan.

SUMMARY OF THE INVENTION

An instrument in accordance with the present invention for the simultaneous measurement of torticollis characteristics, namely head turn, head tilt, and head bend, may include a vertical protractor which provides means for measuring both a patient's head tilt in a sagittal plane of the patient's body and patient's head bend in a frontal plane of the patient's body.

In combination therewith, a horizontal protractor provides means for measuring a patient's head turn in a transverse plane of the patient's body. Particularly, the vertical protractor includes a scale graduated in arcuate degrees in a plane from an ordinal line to an abscissanal line; and a horizontal protractor includes a scale graduated in arcuate degrees from an ordinal line to an abscissanal line.

Additionally, the horizontal protractor is of sufficient size for enabling manual positioning of the horizontal protractor adjacent the vertical protractor at approximately a right angle therebetween with the patient's head disposed between the horizontal protractor and the vertical protractor.

More particularly, the horizontal protractor may include a cutout portion for enabling the horizontal protractor to be disposed under the chin of a patient, and the vertical protractor may include a positionable arrow, which may be rotatably mounted at the intersection of the ordinal and abscissanal lines for indicating either patient head tilt or patient head bend.

Still more particularly, the vertical protractor's scale graduations may include lines extending from the intersection of the coordinate and abscissanal lines to a semicircular line interconnecting the ordinal and abscissanal lines.

Further, the vertical protractor may include a measurement area bounded by the semicircular line and the abscissanal line which is greater than the cross-sectional area of the patient's head in both a frontal plane and a sagittal plane of the patient's head. This feature facilitates the assessment or measurement of head tilt or head bend, as hereinafter described in greater detail.

The vertical protractor area may extend from the intersection of the ordinal and abscissanal lines to the semicircular line. This provides for an arrow length extending significantly past an outline of the patient's head to facilitate accurate measurement of head tilt and head bend.

The horizontal protractor scale graduation may include lines extending from the cutout portion to a semicircular line interconnecting the ordinal and abscissanal lines. Further, the horizontal protractor measurement area, which is bounded by the semicircular line, the cutout portion and the abscissanal line, is greater than the cross-section of the patient's head in a transverse plane of the patient's head. This facilitates measurement of a patient head turn.

A method in accordance with the present invention for simultaneously measuring torticollis characteristics includes the steps of positioning a vertical protractor behind a patient's head and a supporting horizontal protractor adjacent the vertical protractor at approximately a right angle therewith, with the patient's head therebetween.

More particularly, the method includes the step of positioning a patient with a frontal plane of the patient parallel with the vertical protractor and thereafter measuring the patient's head bend in the frontal plane with the vertical protractor and measuring the patient's head turn in the transverse plane with the horizontal protractor.

Specifically, a method in accordance with the present invention may include the alignment of a moveable arrow disposed on the vertical protractor with an angle of the patient's head bend. In addition, the step of measuring the patient's head turn may include positioning a portion of the horizontal protractor under each end of the patient's head.

Alternatively, a method in accordance with the present invention may include the positioning of a patient with the sagittal plane of the patient parallel with the vertical protractor and thereafter measuring the patient's head tilt in the sagittal with the vertical protractor while measuring the patient's head turn in the transverse plane on the patient body with the horizontal protractor.

As with simultaneous measurement of head bend and head turn, the method of simultaneously measuring head tilt and head turn may include aligning a movable arrow disposed on the vertical protractor with the angle of the patient head tilt.

BRIEF DESCRIPTION OF THE DRAWINGS

The advantages and features of the present invention will be better understood by the following description when considered in conjunction with the accompanying drawings in which.

DETAILED DESCRIPTION

Figure 1:
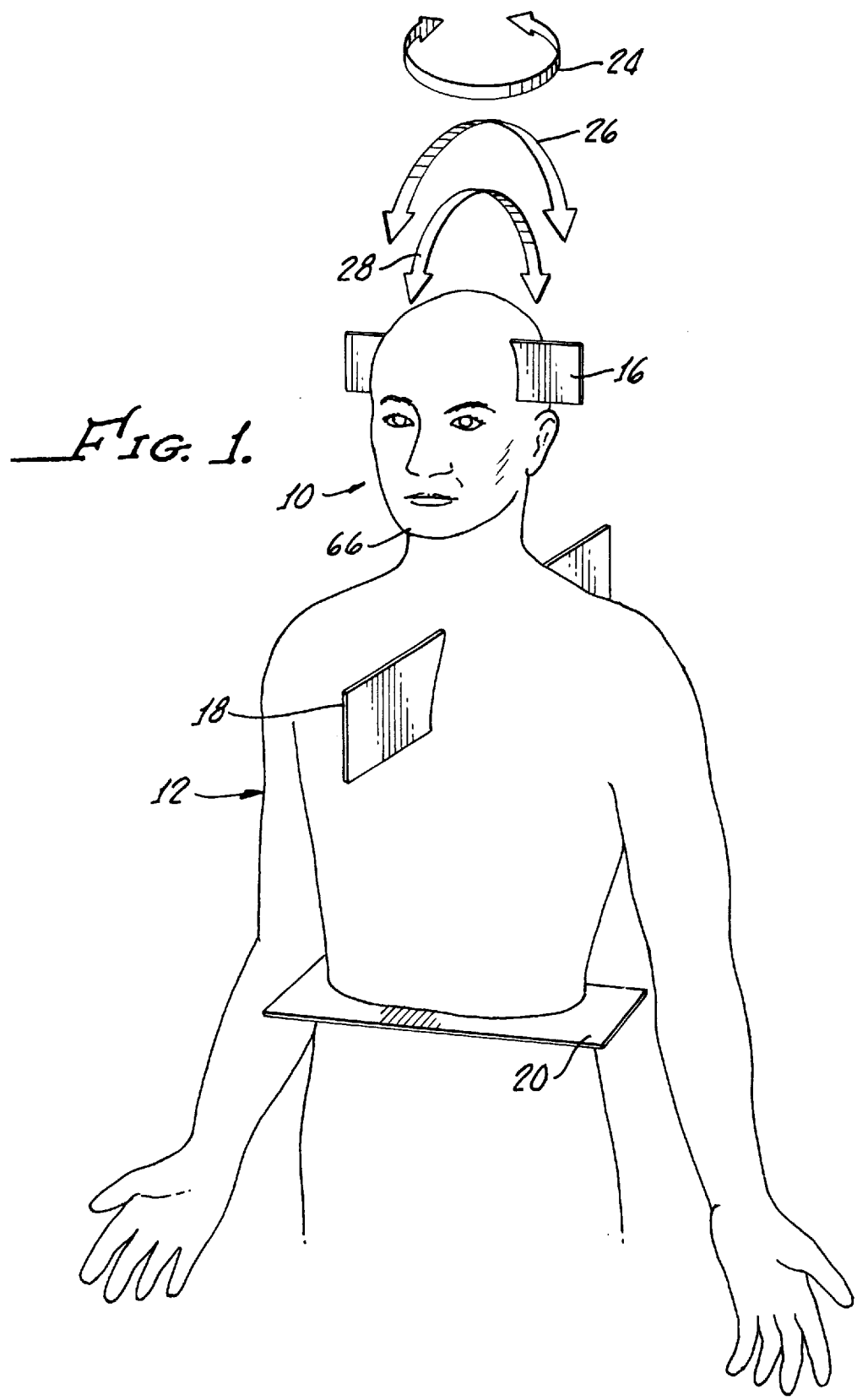
FIG. 1 is a perspective view of a patient's head and body illustrating the frontal, sagittal and transverse planes as utilized in the present specification for describing the head turn (in the transverse plane), head bend (in the frontal plane), and head tilt (in the sagittal plane)

Turning now to FIG. 1, there is illustrated a patient head 10 and a patient body 12, illustrating a frontal plane 16, a sagittal plane 18, and a transverse plane 20, in which torticollis may be measured.

As hereinafter shown in greater detail, head turn is defined by rotation in the transverse plane, as illustrated by the arrow 24; head bend is movement in the frontal plane, as illustrated by the arrow 26; and head tilt in the sagittal plane is illustrated by the arrow 28.

Figure 2:
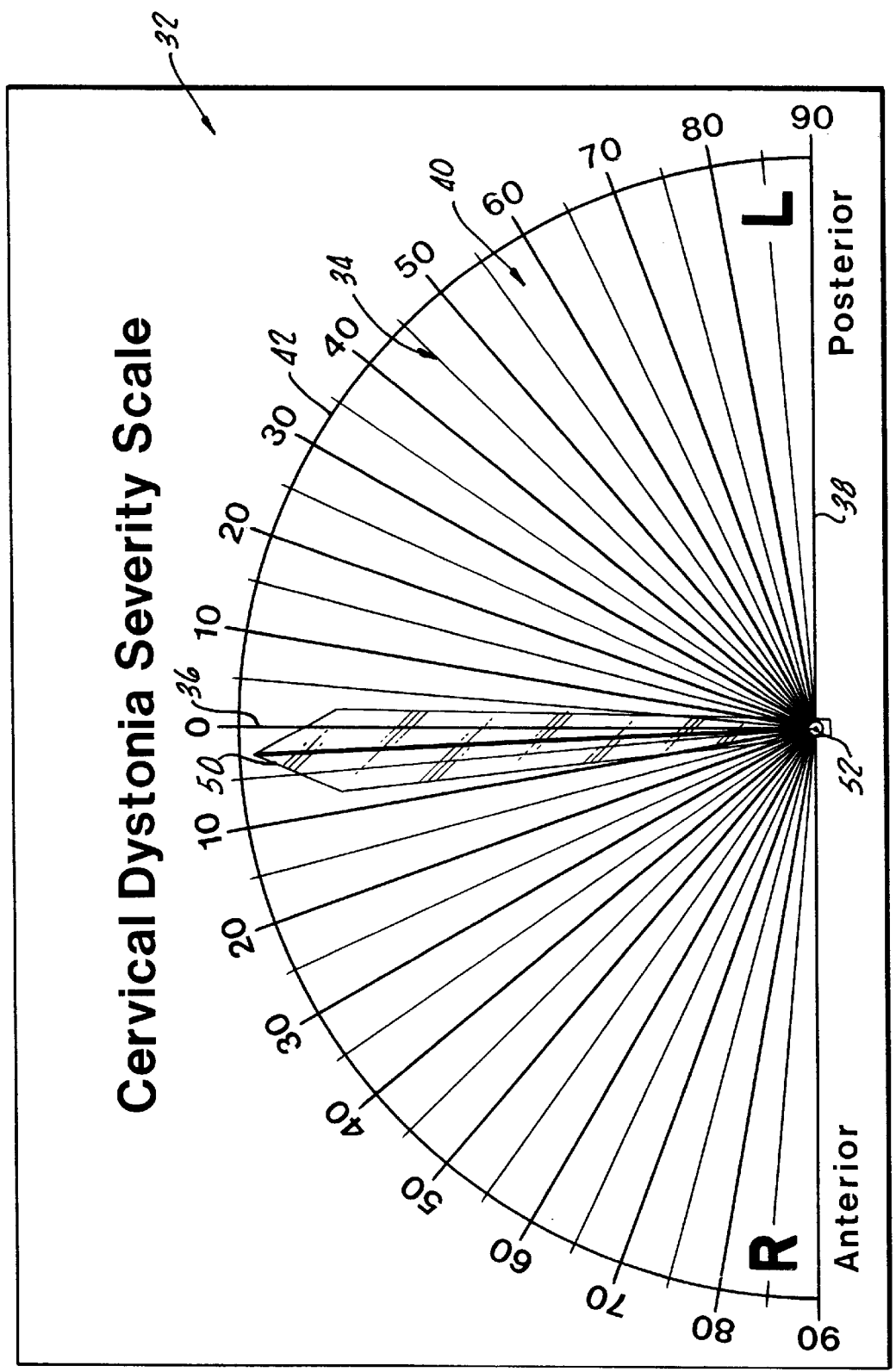
FIG. 2 is a plan view of a vertical protractor in accordance with the present invention.

Turning now to FIG. 2, there is shown a vertical protractor 32 which provides means for measuring both patient head tilt and patient head bend. As hereinafter described, the vertical protractor 32 includes a scale 34 graduated in arcuate degrees in a plane from an ordinal line 36 to an abscissanal line 38.

As will be hereinafter discussed in greater detail, the vertical protractor 32 includes a measurement area 40 bounded by a semicircular line 42 and the abscissanal line 38 which is greater than a cross-sectional area of the patient head 10 in both frontal plane 16 and sagittal plane 18. As hereinafter shown, this facilitates measurement of both head bend and head tilt.

Also shown in FIG. 2 is a positionable arrow 50 rotatably mounted at an intersection 52, the ordinal line 36, and abscissanal line 38, which provides a means for indicating either patient head tilt 28 or patient head bend 26 (see FIG. 1), as will be hereinafter described and illustrated.

Figure 3:
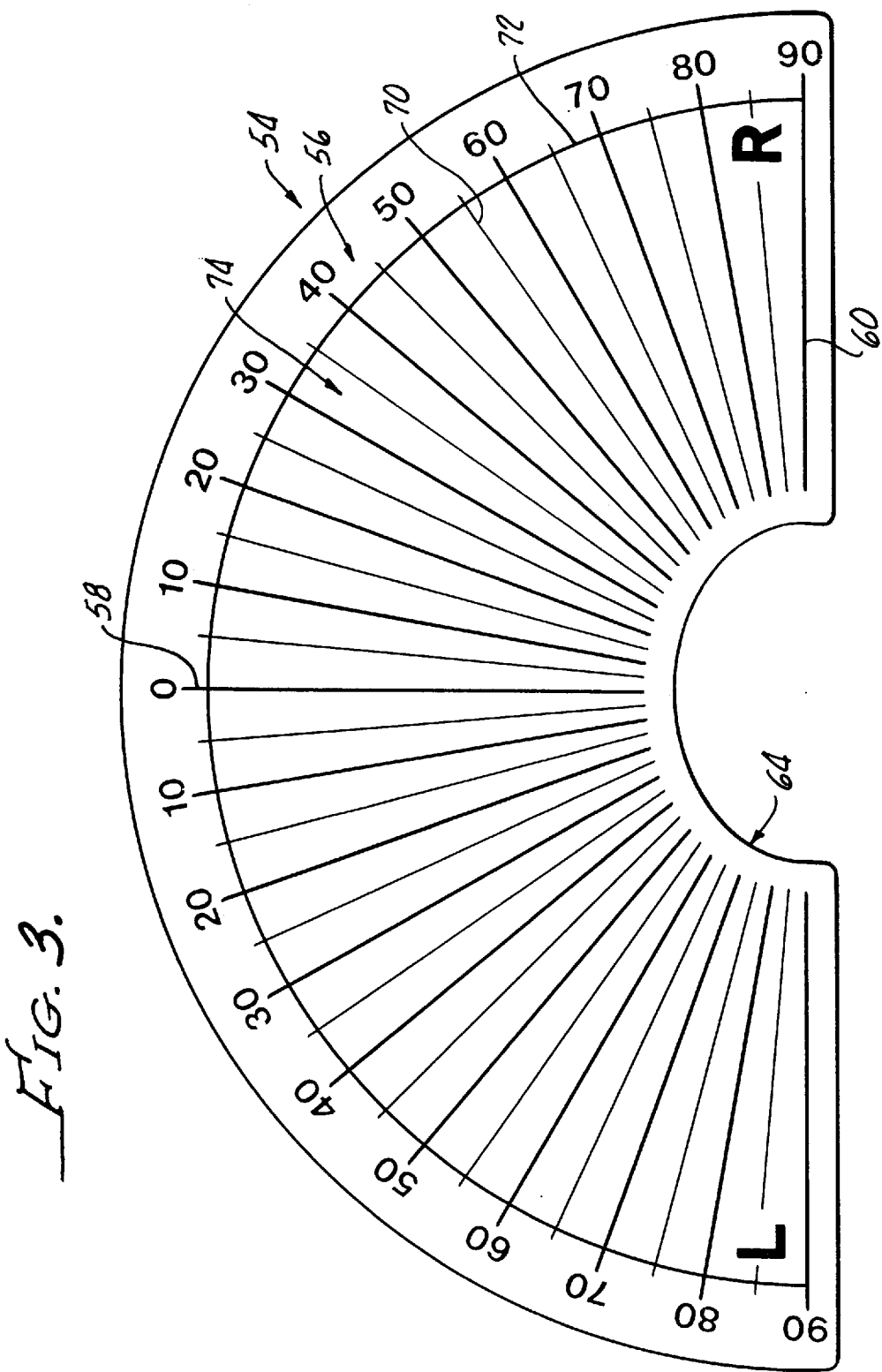
FIG. 3 is a plan view of a horizontal protractor in accordance with the present invention, showing a cutout portion.

Turning now to FIG. 3, there is shown a horizontal protractor 54 which provides means for measuring patient head turn 24 and, in combination with vertical protractor 32, provides a means for simultaneously measuring both patient head turn 24 and patient head bend 26, or patient head turn and patient head tilt 28, as hereinafter described in greater detail.

The horizontal protractor 54 includes a scale graduated in arcuate degrees from an ordinal line 58 to an abscissanal line 60. In addition, a cutout portion 64 provides means for enabling the horizontal protractor to be disposed under a chin 66 of a patient's head 10, as more clearly illustrated in FIGS. 4 and 5.

Figure 4:
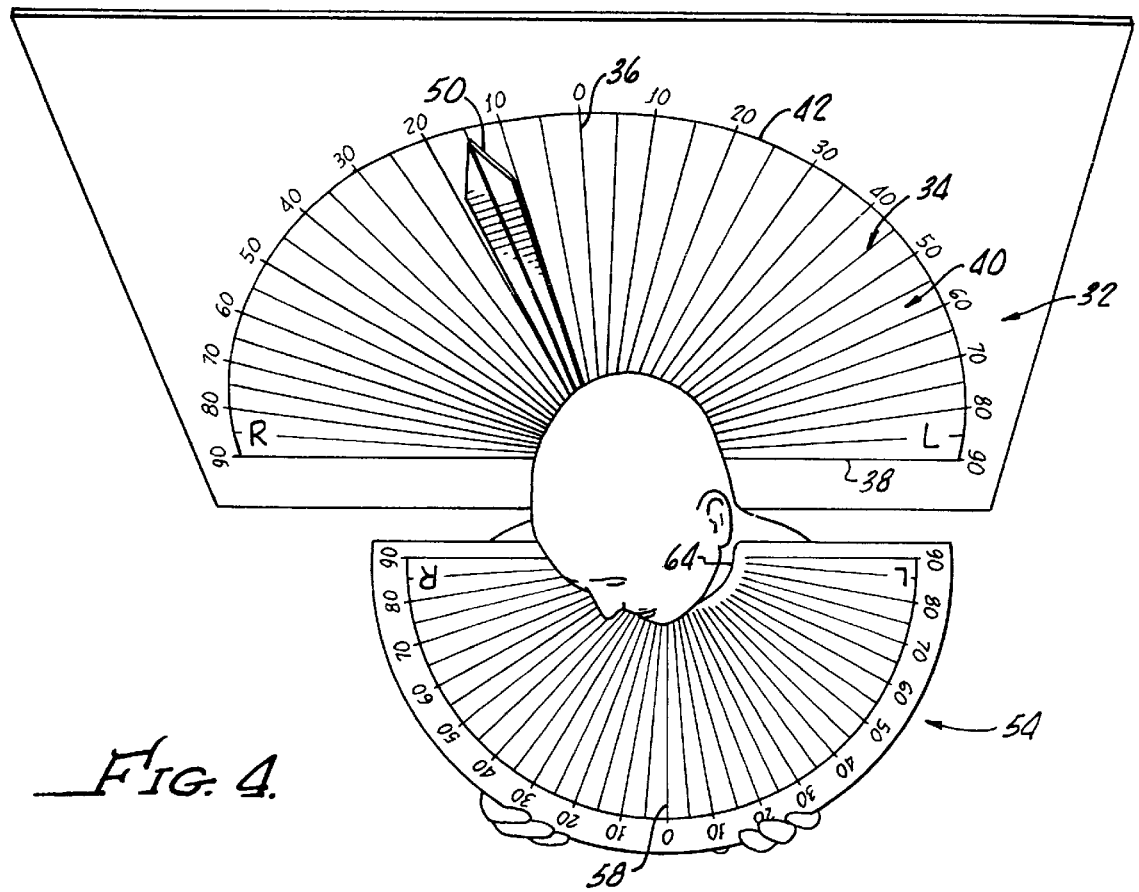
FIG. 4 is an illustration of the vertical and horizontal protractors used in combination for simultaneous measurement of head bend and head turn.
Figure 5:
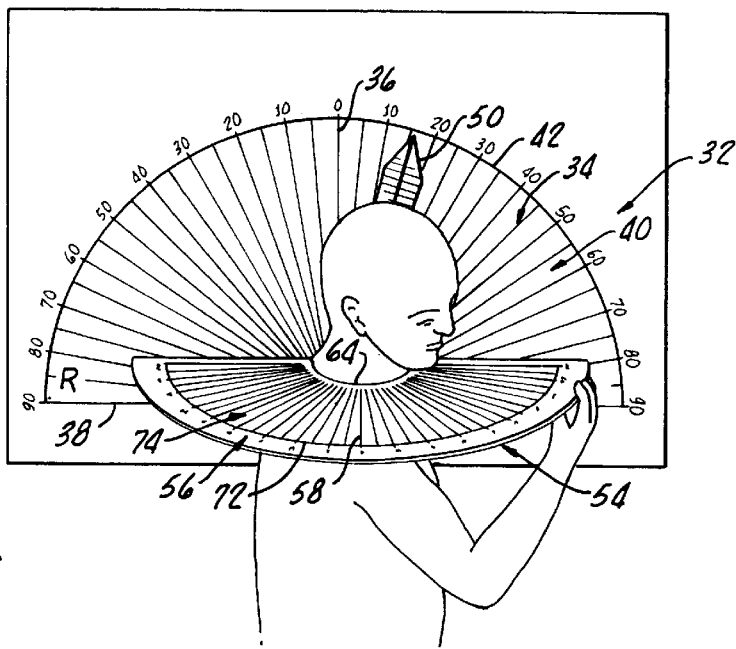
FIG. 5 is an illustration of the vertical and horizontal protractors used in combination for simultaneous measurement of head tilt and head turn.

As also shown in FIGS. 4 and 5, the horizontal protractor 54 is of a size enabling manual positioning of the horizontal protractor adjacent the vertical protractor 32 (see FIGS. 4 and 5) at approximately right angles with the vertical protractor 32 with the patient head 10 disposed between the horizontal protractor 32 and the vertical protractor 54.

As shown in FIGS. 4 and 5, the vertical protractor 32 may be positioned in a vertical alignment behind patient head 10 and the horizontal protractor 54 handheld by the patient. As shown in FIGS. 3 and 5, the horizontal protractor 54 includes scale graduations 70 extending from the cutout portion 64 to a semicircular line 72, intersecting the abscissanal line 60. Further, the measurement area 74, bounded by the semicircular line 72 of the cutout portion 64 and the abscissanal line 60, is greater than a cross-section of the patient's head 10 in the transverse plane 20 in order to facilitate the measurement of head turn 24, shown in FIGS. 1, 4, 5.

Turning again to FIGS. 4 and 5, there is shown a method in accordance with the present invention for simultaneously measuring head bend and head turn (FIG. 4) and simultaneously measuring head tilt and head turn (FIG. 5).

As illustrated in FIG. 4, a method in accordance with the present invention includes positioning a vertical protractor 32 behind a patient's head 10 and supporting a horizontal protractor 54 adjacent the vertical protractor 32 at approximately a right angle therewith, with the patient's head 10 therebetween.

In the simultaneous measurement of head turn and head bend, the patient is positioned with the frontal plane 16 approximately parallel with the vertical protractor 32. Thereafter, the patient head bend in the frontal plane is measured with the vertical protractor utilizing the moveable arrow 52 indicating the angle of the patient's head bend.

Simultaneously, the patient's head turn is measured by observing such head turn against the horizontal protractor 54. It should be noted in this regard that the cutout portion 64 enables the horizontal protractor to be positioned in an almost abutting relationship with the vertical protractor 54. This feature effectively isolates the patient's head 10 so that objective measurement of head turn and head bend may be made without obfuscation by the patient body 12 contortion, if any.

FIG. 5 illustrates a method in accordance with the present invention of the simultaneous measurement of head tilt 28 and head turn 24. Similar to the procedure illustrated in FIG. 4, the vertical protractor 32 is positioned behind the patient head 10, and the horizontal protractor 54 is supported, or positioned, adjacent the vertical protractor, at approximately a right angle therewith, with the patient head 10 therebetween.

In this method, the patient is positioned with the sagittal plane 18 parallel with the vertical protractor 32. Patient head tilt 28 is measured utilizing the movable arrow 50 and patient head turn is measured with the horizontal protractor 54, as hereinabove described.

Although there has been hereinabove described a particular arrangement of an instrument and method for the simultaneous measurement of torticollis characteristics for the purpose of illustrating the manner in which the invention may be used to advantage, it should be appreciated that the invention is not limited thereto. Accordingly, any and all modifications, variations, or equivalent arrangements which may occur to those skilled in the art, should be considered to be within the scope of the present invention as defined in the appended claims.

What is claimed is:

1. An instrument for the simultaneous measurement of torticollis characteristics, namely, head turn, head tilt and head bend, said instrument comprising in combination:

vertical protractor means for measuring both patient head tilt in a sagittal plane of a patient body and patient head bend in a frontal plane of the patient body, said vertical protractor means having a scale graduated in arcuate degrees in a plane from an ordinal line to an abscissanal line; and horizontal protractor means for measuring patient head turn in a transverse plane of the patient body, said horizontal protractor means having a scale graduated in arcuate degrees from an ordinal line to an abscissanal line, said horizontal protractor means further including means, defining a size thereof, for enabling manual positioning of the horizontal protractor means adjacent the vertical protractor means at approximately a right angle therebetween with the patient head disposed between the horizontal protractor means and the vertical protractor means.

2. The instrument according to claim 1 wherein said horizontal protractor means includes means, defining a cut-out portion, for enabling the horizontal protractor means to be disposed under a chin of the patient.

3. The instrument according to claim 2 wherein said vertical protractor means includes positionable arrow means, rotatably mounted at an intersection of the ordinal and abscissanal lines, for indicating either patient head tilt or patient head bend.

4. The instrument according to claim 3 wherein the vertical protractor scale graduations include lines extending from the intersection of the ordinal and abscissanal lines to a semicircular line interconnecting the ordinal and abscissanal lines.

5. The instrument according to claim 4 wherein the vertical protractor means includes a measurement area, bounded by the semicircular line and the abscissanal line, greater than a cross-sectional area of the patient head in both a frontal plane and sagittal plane of the patient head.

6. The instrument according to claim 5 wherein said arrow means extends from the intersection of the ordinal and abscissanal lines to the semicircular line.

7. The instrument according to claim 6 wherein the horizontal protractor scale graduations include lines extending from the cutout portion to a semicircular line interconnecting the ordinal and abscissanal lines.

8. The instrument according to claim 7 wherein said horizontal protractor means includes a measurement area, bounded by the semicircular line, the cutout portion and the abscissanal line, greater than a cross-section of the patient head in a transverse plane of the patient head.

9. A method for simultaneously measuring torticollis characteristics, namely, head turn and head bend, said method comprising the steps of:
  positioning a vertical protractor behind a patient head;
  supporting a horizontal protractor adjacent the vertical protractor at approximately a right angle therewith with the patient head therebetween;
  positioning a patient with a frontal plane of the patient parallel with the vertical protractor;
  measuring patient head bend in the frontal plane with the vertical protractor; and
  measuring patient head turn in a transverse plane of the patient body with the horizontal protractor.

10. The method according to claim 9 wherein the step of measuring patient head bend includes aligning a movable arrow, disposed on said vertical protractor, with an angle of patient head bend.

11. The method according to claim 10 wherein the step of measuring patient head turn includes positioning a portion of the horizontal protractor under a chin of the patient head.

12. A method for simultaneously measuring torticollis characteristics, namely, head turn and head tilt, said method comprising the steps of:
  positioning a vertical protractor behind a patient head;
  supporting a horizontal protractor adjacent the vertical protractor at approximately a right angle therewith with the patient head therebetween;
  positioning a patient with a sagittal plane of the patient parallel with the vertical protractor;
  measuring patient head tilt in the sagittal plane with the vertical protractor; and
  measuring patient head turn in a transverse plane of the patient body with the horizontal protractor.

13. The method according to claim 12 wherein the step of measuring patient head tilt includes aligning a movable arrow, disposed on said vertical protractor, with an angle of patient head tilt.

14. The method according to claim 13 wherein the step of measuring patient head turn includes positioning a portion of the horizontal protractor under a chin of the patient head.

* * * * *